US008864837B2

(12) United States Patent
Hörmansdörfer (10) Patent No.: US 8,864,837 B2
(45) Date of Patent: Oct. 21, 2014

(54) SCREW-IN ELEMENT HAVING CHANGING THREAD PROFILE AND METHOD FOR ITS PRODUCTION (76) Inventor: Gerd Hörmansdörfer, Burgdorf-Beinhorn (DE)

( * ) Notice: Subject to any disclaimer, the term of this patent is extended or adjusted under 35 U.S.C. 154(b) by 1473 days.

(21) Appl. No.: 11/667,248

(22) PCT Filed: Nov. 9, 2005

(86) PCT No.: PCT/DE2005/002013
§ 371 (c)(1),
(2), (4) Date: May 8, 2007

(87) PCT Pub. No.: WO2006/050707
PCT Pub. Date: May 18, 2006

(65) Prior Publication Data
US 2008/0025819 A1    Jan. 31, 2008

(30) Foreign Application Priority Data

Nov. 9, 2004   (DE) .......................... 10 2004 053 944
Nov. 30, 2004  (DE) .......................... 10 2004 057 709
May 30, 2005   (DE) .......................... 10 2005 024 699

(51) Int. Cl.
*A61F 2/34*   (2006.01)
*B23G 1/00*   (2006.01)
*A61F 2/30*   (2006.01)
*F16B 33/02*  (2006.01)

(52) U.S. Cl.
CPC ........... *B23G 1/00* (2013.01); *A61F 2002/3082* (2013.01); *A61F 2/3094* (2013.01); *A61F*
(Continued)

(58) Field of Classification Search
CPC .............. A61F 2002/3041; A61F 2002/30413; A61F 2002/30859–2002/3086; A61B 17/863
See application file for complete search history.

(56) References Cited
U.S. PATENT DOCUMENTS 2,562,516 A    7/1951   Williams
4,653,486 A *  3/1987   Coker ............................. 606/65
(Continued)

FOREIGN PATENT DOCUMENTS

CA    2052978       4/1992
DE    32 35 352     3/1984
(Continued)

OTHER PUBLICATIONS

Two German Search Reports with English translations of both.
(Continued)

*Primary Examiner* — Thomas J Sweet
*Assistant Examiner* — Rebecca Preston
(74) *Attorney, Agent, or Firm* — Collard & Roe, P.C.

(57)  ABSTRACT

The present invention relates to a screw-in element having a changing thread profile, in particular an artificial hip joint socket which may be screwed in, and a method for producing screw-in elements of this type. For the purpose of implementing a specific curve of the thread tooth height along the thread extension, it is suggested that the flank of the thread tooth pointing in the screw-in direction be implemented having a constant angle, and the other flank of the thread tooth be implemented having a changing angle. In addition, it is suggested that a type of staircase function made of ramps and steps be superimposed on the thread course to implement a clearance angle and an exposed position of the thread tooth in this way. The practical implementation of the method requires a CNC machine, preferably a CNC lathe, having a so-called B axis and a specific procedure in regard to the programming. The thread design according to the present invention results, in particular with a self-cutting design, in a reduction of the force required when screwing into tough material.

14 Claims, 6 Drawing Sheets

(52) U.S. Cl.
CPC .......... 2250/0058 (2013.01); *A61F 2230/0017* (2013.01); *A61F 2250/0026* (2013.01); *A61F 2002/30138* (2013.01); *A61G 2220/0033* (2013.01); *A61F 2002/30151* (2013.01); *A61F 2002/30825* (2013.01); *A61F 2002/30952* (2013.01); *A61F 2002/30858* (2013.01); *A61F 2002/30158* (2013.01); *A61F 2002/30535* (2013.01); *A61F 2/34* (2013.01); *A61F 2002/30332* (2013.01); *A61F 2002/30876* (2013.01); *A61F 2002/3085* (2013.01); *A61F 2002/30848* (2013.01); *A61F 2230/0026* (2013.01); *F16B 33/02* (2013.01); *A61F 2002/30322* (2013.01); *A61F 2002/30378* (2013.01)
USPC .................................. 623/22.31; 623/22.27

(56) References Cited

U.S. PATENT DOCUMENTS

| | | | |
|---|---|---|---|
| 4,673,323 A | 6/1987 | Russo | |
| 4,715,859 A | 12/1987 | Schelhas et al. | |
| 4,834,759 A * | 5/1989 | Spotorno et al. | 623/22.3 |
| 4,871,368 A * | 10/1989 | Wagner | 623/22.29 |
| 4,894,064 A | 1/1990 | Imhof | |
| 5,120,171 A | 6/1992 | Lasner | |
| 5,147,407 A | 9/1992 | Täger | |
| 5,458,649 A * | 10/1995 | Spotorno et al. | 623/22.27 |
| 5,628,630 A | 5/1997 | Misch | |
| 5,997,578 A | 12/1999 | Hörmansdörfer | |
| 6,146,425 A | 11/2000 | Hoermansdoerfer | |
| 6,997,711 B2 * | 2/2006 | Miller | 433/174 |
| 7,513,913 B2 | 4/2009 | Hoermansdoerfer | |
| 2003/0153919 A1* | 8/2003 | Harris | 606/69 |
| 2004/0121289 A1 | 6/2004 | Miller | |
| 2005/0038521 A1 | 2/2005 | Hörmansdörfer | |
| 2007/0099153 A1* | 5/2007 | Fromovich | 433/174 |
| 2009/0165611 A1 | 7/2009 | Hormansdorfer | |

FOREIGN PATENT DOCUMENTS

| | | |
|---|---|---|
| DE | 33 25 448 | 1/1985 |
| DE | 32 42 926 | 2/1986 |
| DE | 36 02 081 | 10/1986 |
| DE | 35 35 959 | 4/1987 |
| DE | 94 02 828 U1 | 7/1994 |
| DE | 298 14 010 U1 | 11/1998 |
| DE | 197 57 799 A1 | 7/1999 |
| EP | 0 358 345 A1 | 3/1990 |
| EP | 0 480 551 | 4/1992 |
| EP | 0 622 058 A2 | 11/1994 |
| EP | 0 687 165 | 12/1995 |
| EP | 0 898 470 | 3/1999 |
| EP | 1 051 131 | 11/2000 |
| EP | 1 318 803 | 6/2003 |
| FR | 1 118 057 | 5/1956 |
| FR | 2 548 012 | 1/1985 |
| FR | 2 622 432 | 5/1989 |
| JP | 61-217159 | 9/1986 |
| JP | 01-155845 | 6/1989 |
| JP | 07217635 | 8/1995 |
| JP | 2001-502194 | 2/2001 |
| JP | 2004-011678 | 1/2004 |
| WO | WO 95/18586 | 7/1995 |
| WO | WO 97/39702 | 10/1997 |
| WO | WO 99/33416 | 7/1999 |
| WO | WO 00/75737 | 12/2000 |
| WO | WO 02/09688 | 7/2002 |

OTHER PUBLICATIONS

International Search Report.
DIN 58 810, Mar. 1984, p. 363.

* cited by examiner

Prior Art

SCREW-IN ELEMENT HAVING CHANGING THREAD PROFILE AND METHOD FOR ITS PRODUCTION

CROSS REFERENCE TO RELATED APPLICATIONS

Applicant claims priority under 35 U.S.C. §119 of German Application No. 10 2004 053 944.8 filed Nov. 9, 2004, German Application No. 10 2004 057 709.9 filed Nov. 30, 2004, and German Application No. 10 2005 024 699.0 filed May 30, 2005. Applicant also claims priority under 35 U.S.C. §365 of PCT/DE2005/002013 filed Nov. 9, 2005. The international application under PCT article 21(2) was not published in English.

The present invention relates to a screw-in element having a lateral surface which is nonlinear in at least one partial area, in particular buckled or curved, and a thread lying at least in this partial area having a changing thread profile formed by thread tooth and thread groove, the flank of the thread tooth lying in the screw-in direction having a constant angle. Furthermore, the present invention relates to a method for machining threads, which have a thread profile which changes at least in a partial area, on a CNC machine, preferably a CNC lathe, the thread being machined using at least two production steps and/or cycles at least in this partial area.

Threads are widely distributed as constructive elements of general mechanical engineering. Threads are typically shaped cylindrically. In addition, conical threads, e.g., for oil field pipes, are also in use. A large number of various thread profiles are known and defined in standards. The thread profile on a workpiece is typically unchanging, i.e., the thread profile at the thread beginning is identical to that at the thread end. However, exceptions are conceivable, in which a shape design of the thread profile formed by thread groove and thread tooth which changes flowingly may be advantageous in at least a partial area of the thread, e.g., to make the insertion of a screw thread into a nut thread easier.

Special geometric conditions in regard to the thread exist above all, however, in threads on curved surfaces, as occur in particular in artificial hip joint sockets which may be screwed in. For example, hypospherical, hemispherical, or hyperspherical, conical-spherical, parabolic toroidal, elliptical, and similar geometries are known in regard to the exterior shape of the shell body. In machining methods for producing screw-in sockets of this type, flowingly changing distortions of the thread profile partially automatically result, which are neither intended nor desired in most cases. In particular if thread teeth having asymmetrical flanks (the particular lateral angles of the thread tooth profile) are used, the phenomenon results that depending on the tilting direction of the resulting thread tooth, the tooth height from the socket equator increases or decreases flowingly in the direction toward the socket pole, because of which thread teeth which are either much too large or nearly stunted result at the thread beginning near the pole. In the first case, the extremely large thread teeth result in very high forces being necessary for screwing in the socket, and/or the implant not being able to be screwed in up to complete bone contact. In the second case, only a very poor primary fixation will be achieved. In both cases, the danger of loosening of the implant exists, which would mean another operation on the patient as a consequence.

Figure 6:
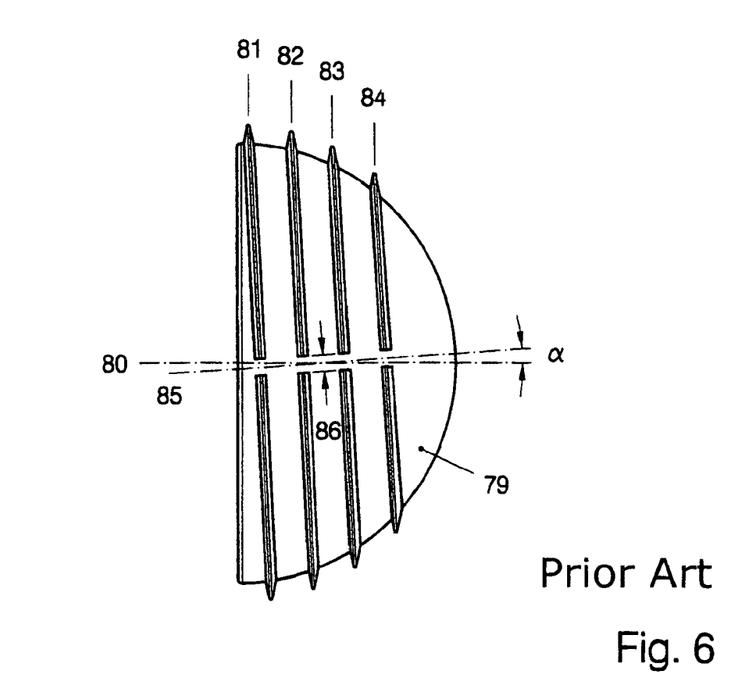
FIG. 6 shows an artificial hip joint socket having a thread according to the prior art.

A threaded socket is known from French Patent Application 2 548 012, whose external shape is described in the application text as cylindrical-spherical. It is equipped with a single-start thread, which extends over the entire external length and whose thread profile changes flowingly from the socket equator toward the socket pole. This profile change is expressed in a decrease of the tooth height and an increasing inequality of the tooth flank lengths in the direction toward the socket pole. The thread is manufactured as a typical ISO thread having an enclosed flank angle of 60°. The result of the last step using a typical tool (e.g., thread cutting insert) is more or less shown in the figures of the drawing. For the purpose of achieving a constant thread pitch in regard to the thread tooth peaks, it is suggested that the tool be moved on a path having a pitch which changes upon each revolution during the production on a CNC machine. The geometrical background for ascertaining the particular pitch is illustrated in FIG. 6 of the cited application. At first view, the specified procedure appears plausible and implementable without further measures.

Upon closer analysis, it is first notable that the thread peaks and the particular thread base lie on circular arcs in the two-dimensional illustration, but their center of rotation is not coincident with the socket axis. Therefore, a spherical shape is not implemented for the thread base or for the geometrical mantle enveloping the tooth peaks. A precise drawing using a CAD system proves that the visually examined production methods are in no way capable of implementing the thread tooth profile illustrated. Specifically, severe geometric effects arise with increasing plunging of the thread groove toward the socket pole, which results in extreme fluctuations of the thread tooth height. These drastic flaws are not visible in the figure of the drawing of the application, which is produced by hand, because they are balanced out by a summation of a large number of drawing irregularities.

It is not actually possible, however, to follow multiple regularities which are independent one another using the unchanging thread profile of a tool which cuts the thread during a single-pass final cut.

In addition, the suggested thread having an ISO profile is unsuitable for the intended purpose in any case, because it does not take into consideration the strength ratio between the bone and the implant material and, in addition, it requires very high screw-in forces during implantation. Even if the thread profile is altered, e.g., by using a lathe chisel having a trapezoidal profile and an accompanying narrowing of the thread teeth, the thread base would be represented by steps in the event of a single-pass production method. Therefore, not only would jamming effects be connected with the screwing in, but rather also undesired gap formation in the contact area to the bony bearing surface. These problems exist in principle for many types of screw-in elements which have a lateral surface at least partially curved in a partial area and, in addition, are screwed into a material having a significantly reduced strength in relation to that of the screw-in element.

The state of affairs described above is the subject matter of European Patent Specification EP 0 687 165, and is therefore generally known. It is suggested in this specification that the thread be machined having different pitches to achieve a specific thread profile curve. This method has already been successfully applied in the field of medical technology for producing bone screws and artificial hip joint sockets. The protective rights of the associated patent family are exclusively used by the particular producer in regard to the particular product group. However, the bandwidth of design possibilities available with the method is restricted to the use of various thread pitches. Influencing the tilt angle of the thread tooth in any way is not possible.

A hip joint socket having a self-cutting thread and a cambered contour of the shell mantle is known from Published Application DE 33 25 448, which in principle has a constant profile of the thread tooth having perpendicular positioning on a tangent applied to the shell mantle. Accordingly, both flanks of the thread tooth are subject to a synchronously increasing tilt in the direction toward the socket pole. The tooth peaks project out of the shell mantle at an identical height in each case on the angle bisector. This thread is produced with the aid of a multi-axis milling machine.

However, a careful examination of the screw-in situation existing in the cited threaded socket using a 2D simulation on a computer shows that a thread design of this type cannot function optimally. The essential flaw is the occurrence of a gap on at least one side between the thread tooth and the bony bearing surface, because a furrow is generated during the screwing process which is wider than the thread tooth profile itself.

Therefore, the object exists of providing alternative screw-in elements (e.g., in the form of bone screws or hip joint sockets), which are producible by machining on a CNC lathe, having a thread lying in at least one partial area on a curved or angled lateral surface having asymmetrical flanks of the thread tooth and a thread tooth height which is adaptable along the thread extension, as well as a method for producing such a special thread for this and other applications on a CNC machine, preferably on a CNC lathe.

In a screw-in element having a lateral surface which is nonlinear, in particular buckled or curved in at least one partial area, and a thread lying at least in this partial area having a changing thread profile formed by thread tooth and thread groove, the flank of the thread tooth lying in the screw-in direction having a constant angle, it is essential to the present invention that the other flank of the thread tooth is subject to an angle change in the cited partial area.

In a preferred embodiment of the present invention, the flank of the thread tooth lying in the screw-in direction is oriented sub-vertically, preferably perpendicularly, to the axis of the screw-in element. Furthermore, it is favorable for the angle change of the other flank to occur continuously, in particular essentially flowingly. The thread teeth are favorably implemented in such a way that a geometric function formed by at least one ramp function and one step function each is superimposed on the curve of the thread teeth. In addition, in a preferred embodiment, the height of the thread tooth profile is reduced in relation to the lateral surface of the screw-in element in the area lying behind a particular tooth cutting edge. The tooth cutting edge of each tooth is preferably implemented as projecting on the equator side in comparison to the tooth cutting edge of the preceding tooth. Good cutting behavior is achieved by lateral offset. The screw-in element is preferably implemented as an implant and particularly preferably as an artificial hip joint socket.

Furthermore, it is favorable for the thread groove of a thread lying on an at least partially curved or angled lateral surface of a screw-in element to be divided into at least two strip-shaped partial surfaces, the first of which is formed by the flank of the thread tooth pointing toward the socket pole and the second of which is formed by the flank of the thread tooth pointing toward the thread equator, and the first flank is unchanging in its angle along the thread extension, while the second flank has an angle change in at least one partial area along the extension of the thread, by which the height and/or the tilt angle of the thread tooth is tailored to the constructive task. Furthermore, a method for producing such a special thread on a CNC machine, such as a CNC lathe, preferably having tool drive, is provided by the present invention.

The method according to the present invention for machining threads having a thread profile changing in at least one partial area on a CNC machine, preferably a CNC lathe, the thread being machined using at least two production steps and/or cycles at least in this partial area, is distinguished in that in one of these production steps and/or cycles, the edge of the lathe chisel which cuts the thread tooth flank assumes a fixed angle, and in the other production step and/or cycle, the edge of the lathe chisel which cuts the other thread tooth flank is changed in its angle during the passage through the thread groove.

In a further embodiment of the method according to the present invention, one machining step and/or cycle essentially relates to one flank of the thread tooth and one part of the neighboring thread base and the other machining step and/or cycle essentially relates to the other flank of the thread tooth and a part of the thread base neighboring this other flank. It is especially favorable for the thread to be machined using three different machining steps and/or cycles, in which essentially the middle of the thread groove is machined using the third machining step and/or cycle and an angle setting is used for the lathe chisel in this case which lies between the angle setting is used for the two other machining steps and/or cycles. The third machining step is especially preferably executed first. It is also favorable for the method if the angle change of the lathe chisel cutting the other thread tooth flank is performed continuously, in particular essentially flowingly, during the passage through the thread groove. In another aspect, the angle change of the lathe chisel is implemented by rotation of the B axis of the CNC machine, preferably of a CNC lathe. In a special embodiment of the method, firstly the path to be described by the cutting radius center point of the lathe chisel during the start of the lateral surface, to be implemented in the form of the thread groove base, of the screw-in element to be produced is calculated, this path is converted using a particular offset for X and Z in relation to the distance of the cutting radius center point of the lathe chisel from the rotation center point of the B axis of the compound slide and for B in relation to the angular difference between the blade of the lathe chisel and the zero setting of the B axis and applied in the CNC program, and a cutter center line is used in the workpiece description whose absolute value corresponds to the cutting radius of the lathe chisel. In a further aspect of the method, a ramp and step function synchronized with the tooth sequence is superimposed on the relative movement between workpiece and tool. This chip removal favorably occurs using milling.

It is suggested that the thread groove be machined along the contour formed by the lateral surface of the screw-in element (this is the base of the thread groove in principle) in the area provided for adapting the thread profile in at least two production steps, one machining step essentially generating the flank pointing toward the socket pole and a further machining step essentially generating the flank of the thread tooth pointing toward the socket equator, and the partial flank angle being changed at least in a partial area of the thread extension for the flank pointing toward the socket equator.

For the practical execution of the method, e.g., on a CNC lathe, alternately either the same tool or two or more tools may be used. If only one tool is to be used, its tool cutting edge must be positioned having its angle in such a way that it corresponds to the partial flank angle of the thread tooth. A reversible tip made entirely of sintered carbide is typically used as a tool for machining of this type, which encloses a specific included angle (e.g., 35°, 55°, or 75°) because of a standardized geometry. The reversible tip would then stand on a neutral holder having its angle bisector perpendicular to the axis of the thread. In relation to the angle bisector, the angle of the tool cutting edge would thus correspond to half of the included angle. Known methods for fixed adaptation of the tool cutting-edge angle comprise either milling the holder appropriately, inserting spacers, or chucking it diagonally. A significantly more elegant method is applicable using the present invention if, for example, a CNC lathe having a controllable B axis of the compound slide is available. The holder having the reversible tip may be brought into the desired angle using appropriate programming of the B axis. This angle, which is to be classified as static, may be set to another angle absolute value after every single passage during thread cutting, for example. However, to implement the dynamic angle displacement according to the present invention, it is necessary to alter the B angle during the passage of the tool through the thread groove. For example, one of the partial flank angles of a thread tooth may have an absolute value of 20° at the beginning of the thread and 12° at the end. The possibility is opened up by the programmable pivoting of this angle, which is alternate in regard to the right and/or left flank and is continuous to sudden, of adapting both the height and also the tilt angle of the thread tooth nearly arbitrarily, i.e., flowingly, to the constructive tasks.

The present invention allows the selection here of either using a tool whose profile corresponds to the profile of the thread groove at its narrowest point, or a tool which is generally narrower than the thread groove. In the second case, for the thread cutting, in addition to using at least one changing partial flank angle for the machining steps, a correspondingly adapted offset value may also be incorporated in the pitch axis to compensate for the difference between tool and thread groove widths. This procedure is especially advantageous because, for example, a smaller tip rounding of the machining tool is thus made possible. Thus, if a small relative offset of the tool is used after each pass of a thread cutting cycle, the thread base may be more finely resolved and the curved or buckled lateral surface may be adapted better.

Furthermore, the possible selection is offered by the present invention of performing the thread machining using more than two production steps, and/or using two or more tools. For example, if three production steps are applied, it is recommended that essentially one side of the thread groove be machined during one of the production steps, essentially the other side of the thread groove be machined in a further step, and essentially the thread base be machined in a third production step. A positioning is selected for the tool which cuts the sides of the thread groove and thus the particular flanks of the thread teeth which results in the particular partial flank angle, while it is suggested that a positioning whose angle lies between these two positions be used for the tool cutting essentially in the middle of the thread base. It is thus possible with increasing number of machining steps and/or tools, with correspondingly smaller rounding of the particular tool tip, to achieve a relatively small rounding of the thread tooth base and even better adaptation of the thread base to the desired contour of the lateral surface of a screw-in element of this type.

The method according to the present invention is intended for use on a machine controlled by computer, in particular a CNC lathe. During thread turning on machines of this type, it is typical to machine the thread groove in multiple passes using a lathe chisel. The production step is referred to as a thread cutting cycle. Only a small amount of material is removed during a single pass, but high feed rates may be used. In contrast, a production step in thread milling may comprise a single pass, because of which, due to the small feed rate required, a significantly higher time outlay typically results in comparison to turning, however. In any case, only those CNC machines and/or CNC lathe which have a pivot axis for the tool in the plane formed by the longitudinal axis (Z) and radial axis (X) of the workpiece are suitable for manufacturing the thread according to the present invention. The path to be covered by the particular tool and/or for the particular cycle in relation to the workpiece must be stored in the corresponding CNC program. For synchronizing the production steps and/or tools it is necessary to calculate the different starting points for the individual production steps and/or cutting cycles precisely and input them. Besides the typical parameters, the values according to the angles for the above-mentioned pivot axis (B) must additionally be stored in the program sets.

During the production of a screw-in element according to the present invention on a CNC lathe, a specific procedure is indicated. For this purpose, the thread groove is first cleared out coarsely using a suitable parting tool. A first shorter thread cycle may then be executed, in which a finishing chisel is advanced toward the depth in the X axis until the thread base is reached—preferably in its center. This finishing chisel is subsequently advanced in the Z axis in each cut of the thread cutting cycle by the absolute value of the chip thickness until the corresponding flank of the thread groove is completely produced. The cutting flank of the lathe chisel must correspond in its angle to that of the thread tooth flank. This is true correspondingly for the thread tooth flank on the other side of the thread groove. This angle is adjustable very simply via the programming of the B axis in regard to the cutting edge of the lathe chisel. The same lathe chisel may be used in this way on both sides to be machined. This also has the advantage that complex synchronization of the chisel tips, which would be necessary in the event of two tools, may be dispensed with.

Because automatic compensation of the cutting radius is not possible during thread cutting in the CNC lathes according to the prior art, a trick must be used here to be able to produce the contour of the workpiece mantle formed as the thread groove base without distortion. For this purpose, the cutting radius center point of the particular tool is described in the tool file and a contour of the workpiece enlarged by a cutter center line having the distance of the cutting radius is programmed.

A similar procedure must be used if a function for automatic correction with dynamically pivoting B axis—referred to sometimes as ATC (automatic tool correction)—is not provided in the program of the machine. Without such a correction, because of the traveling B angle, the position of the lathe chisel tip would change continuously and move away from the correct position. The workpiece would then assume scurrilous shapes and no longer correspond to the target geometry. Therefore, it is hereby suggested that the rotation center point of the B axis of the compound slide of the machine be used in the programming, and not, as is typical, the blade radius center point of the lathe chisel. For this purpose, the distance of this rotation center point from the particular blade radius center point of the lathe chisel is determined and the lengths for the side adjacent and side opposite are calculated from this hypotenuse. The correction triangle thus calculated must only be pivoted around the correction angle, which is enclosed between the cutting flank of the lathe chisel and the X axis of the compound slide. The correct position of the rotation point of the B axis is determined by the intersection point between side opposite and hypotenuse.

BRIEF DESCRIPTION OF THE DRAWINGS

For better understanding, the screw-in element according to the present invention and also the method according to the present invention will be explained in the following on the basis of schematic examples with the aid of eight figures of the drawing. A hip joint socket shown in simplified form is used as an example of a screw-in element having a curved lateral surface. FIG. 2 shows such a hip joint socket having a constant length of the pole-side tooth flank, while FIG. 3 shows an advantageous embodiment, in which the angle bisectors lying between the thread teeth have a constant height. The schematic development of two thread teeth of a thread course having a pivoting partial flank angle is shown in FIG. 4, while

Figure 1:
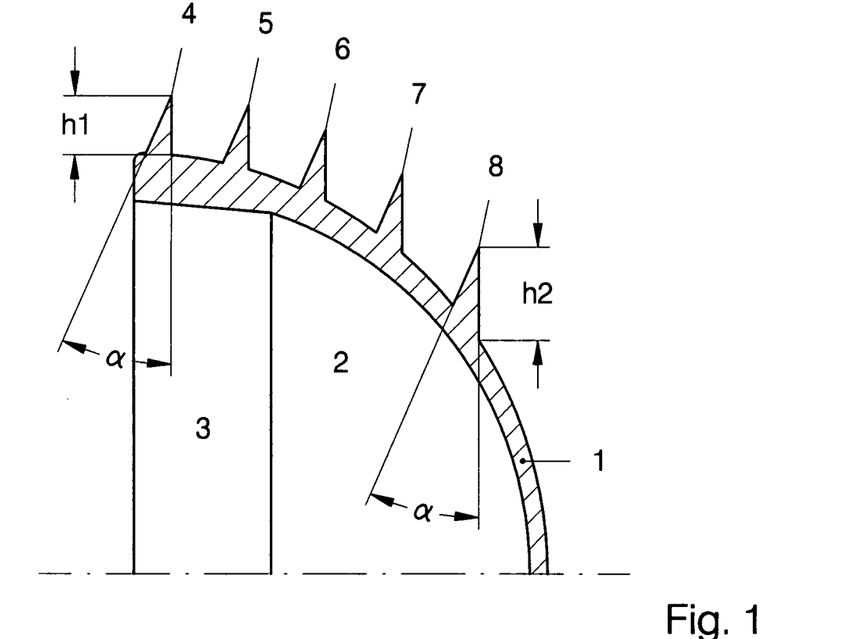
FIG. 1 shows an artificial hip joint socket having a thread according to the prior art.

FIG. 1 is to illustrate the phenomenon described above, which results in a stronger fluctuation of the thread tooth height in the event of curved lateral surfaces of rotation bodies having a tilted profile of the thread teeth. For illustration, a somewhat simplified exemplary embodiment of an artificial hemispherical hip joint socket of moderate size having a conventionally produced screw thread is used in a sectional illustration of one side in a scale of approximately 2.5:1. A value of 5.2 mm was selected for the thread pitch. The thread teeth are shown significantly exaggerated to make the details better visible. In addition, they were shown as running to a tip at the tooth head and without rounding of the tooth base for the sake of simplicity, although in practical embodiments the tooth head is trimmed and the tooth base is provided with a transition radius.

The hip joint socket 1 is formed by a shell having a hemispherical external shape, whose internal contour is divided into an area of a spherical section 2 and a conical section 3. This internal area is provided for receiving a liner. The five thread teeth 4, 5, 6, 7, 8 have an asymmetrical profile. Their flanks pointing toward the pole of the socket have an angle of 0°, and their flanks pointing toward the equator of the socket have an angle of 24°. Accordingly, the enclosed flank angle $\alpha$ is 24°, through which a tilt angle of the angle bisectors of 12° in the direction toward the socket pole results. This tilt direction of the thread teeth is especially favorable for the intended use in an artificial hip joint socket, because due to the predefined main load direction, better force introduction conditions into the human pelvis may be achieved.

Figure 8:
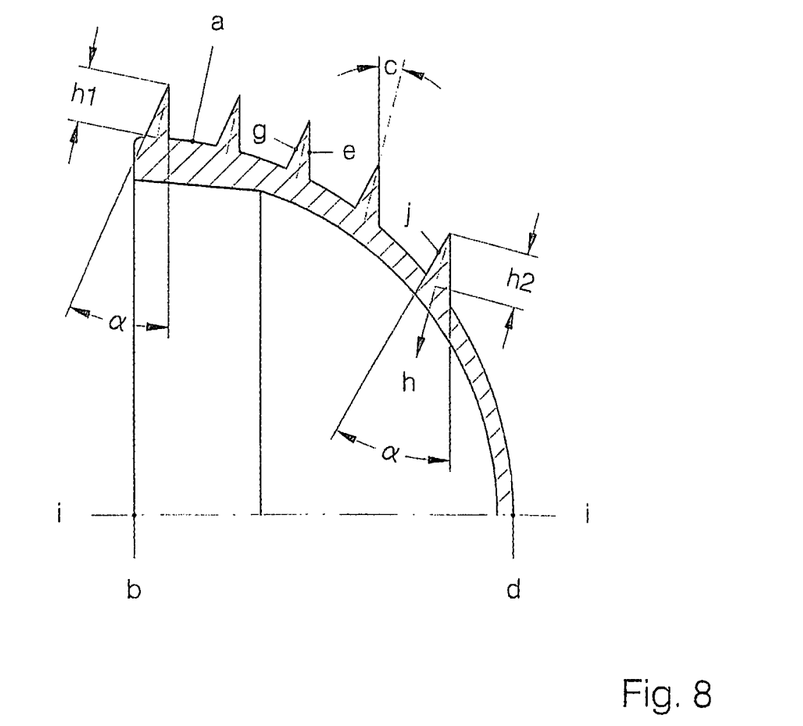
FIG. 8 shows an artificial hip joint socket illustrating the thread groove, the equator, the tilt angle, the socket pole, the flank of the thread lying in the screw-in direction, the second flank of the thread tooth, the sub-vertical direction, the axis of the screw-in element, and the cutting edge of the tooth.

In the example shown, the lateral surface of the socket shell follows the spherical shape with high precision. However, this is only present in the area of the thread groove a (FIG. 8). An implementation of this type requires special machining methods, in which typically passes using two or more lathe chisels having different front and/or side angles and different paths and/or relative displacements of the particular lathe chisel position are necessary. Methods of this type are known, for example, from EP 0 480 551 B1 and EP 0 687 165 B1. However, because the thread is cut having constant pitch and constant partial flank angles, a flowing change of the thread tooth height results from the tilt angle c (FIG. 8) of the thread teeth. It may be seen well in FIG. 1 that the radially measured thread tooth height h2 in proximity to the pole d (FIG. 8) is almost twice as large as the thread tooth height h1 in proximity to the equator b (FIG. 8). Although flowing increases or decreases of the thread tooth height may be completely desirable up to a certain degree in artificial hip joint sockets in particular and various arguments have also been put forth for this purpose, such a strong increase of the thread tooth height is extremely disadvantageous, because there is thus an unnecessarily deep engagement in the bone material. Thread teeth this large at the thread beginning in proximity to the pole also result, in particular in self-cutting threaded sockets, in very high screwing forces, because the chip removal work during screwing into the pelvis is distributed onto only a few tooth cutting edges in the area of the abrupt rise of the thread tooth height at the thread beginning. The screwing of the hip joint socket up to complete bone contact may thus be put into question.

Figure 2:
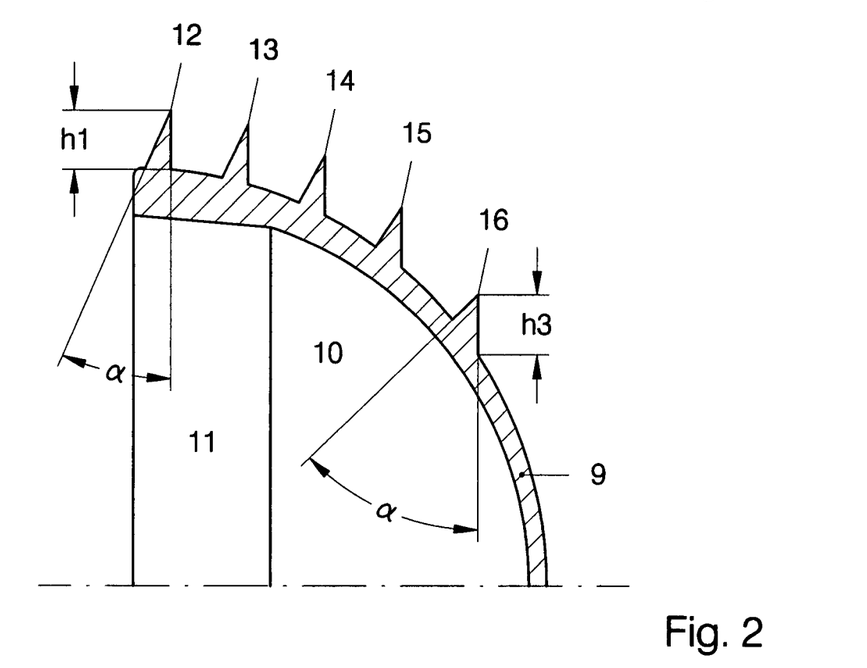

FIG. 2 shows, in a mode of illustration identical to FIG. 1, the simplified and slightly distorted exemplary embodiment of an artificial hip joint socket having a screw thread according to the present invention. The hip joint socket 9 shown corresponds in its inner contour made of spherical section 10 and conical area 11 and the number of the thread teeth 12, 13, 14, 15, 16 to that from FIG. 1. The thread tooth 12 in proximity to the equator of the hip joint socket has a shape and absolute value of its height h1 which are identical to the corresponding thread tooth 4 from FIG. 1. The thread base lying between the teeth represents the spherical shape of the shell lateral surface, as before. Because of the machining of the thread according to the present invention using two production steps, the flank of the thread tooth pointing toward the equator being cut having a flowingly changing angle, a radially measured tooth height h3 is implemented for the thread tooth 16 in proximity to the pole which corresponds to the tooth height h1 of the tooth 12 in proximity to the equator. However, the enclosed flank angle $\alpha$ of the thread tooth has increased from 24° to approximately 46°. This extremely robust enlargement of the flank angle was solely selected here to be able to better illustrate the principal of the design and machining according to the present invention.

Figure 3:
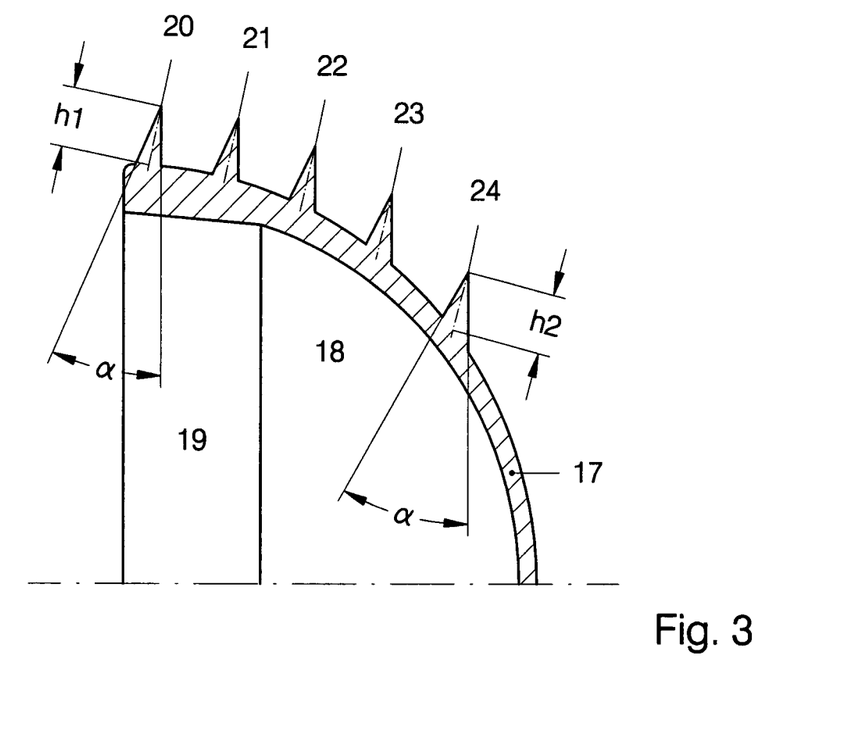

FIG. 3 shows a variation of an artificial hip joint socket which comes significantly closer to a practical embodiment. The figure of the drawing shows, in the way already known from the preceding figures, the sectional image of a threaded socket 17 of hemispherical design, whose interior space is formed by a spherical section 18 having an adjoining conical area 19. The threaded socket is equipped with a thread from which five thread teeth 20, 21, 22, 23, 24 result in the sectional image. The angle bisectors are shown in the particular tooth profile as dot-dash lines. For the tooth profile of the thread tooth 20 having an enclosed flank angle $\alpha$ of 24°, the tilt angle of this angle bisector is 12° in the direction toward the pole. For the thread tooth 24, which has an enclosed flank angle $\alpha$ of approximately 30°, the tilt angle of the angle bisector accordingly has increased to approximately 15° in the direction toward the pole. In all cases, the flanks of the thread teeth pointing toward the socket pole d (FIG. 8) each stand perpendicularly or in a sub-vertical direction h (FIG. 8) on the socket axis, i.e. to the axis of the screw-in element i (FIG. 8). The tooth heights measured along the angle bisectors, which are shown both for the thread tooth 20 by h1 and also for the thread tooth 24 by h2 in the figure of the drawing, are each equally large.

Exemplary embodiments were shown in FIGS. 2 and 3 of the drawing in which, using the method according to the present invention, a specific section of the tooth profile has been brought to a constant length. The suggested method is not restricted thereto, however. On the contrary, through a specific establishment of a jumping and/or sliding pivot of the cutting edge of the lathe chisel and a corresponding programming of the B axis of the CNC machine, it opens up numerous variation possibilities, by which not only exactly determinable increases or decreases of the thread tooth height, but rather also favorable clearance angles and/or cutting angles on the thread teeth may be implemented. These modifications are also partially usable in partial areas of the thread.

Figure 4:
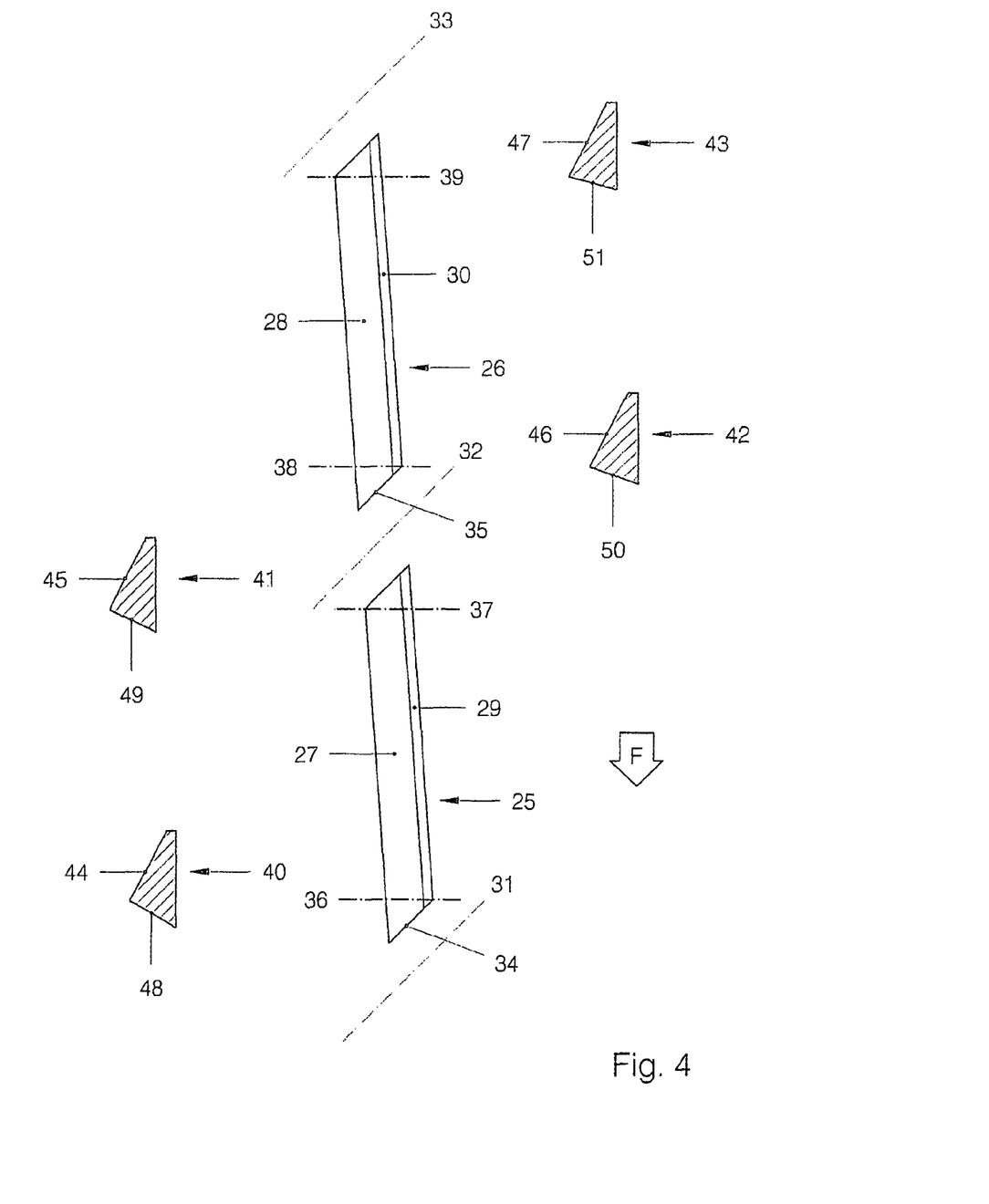
Figure 5:
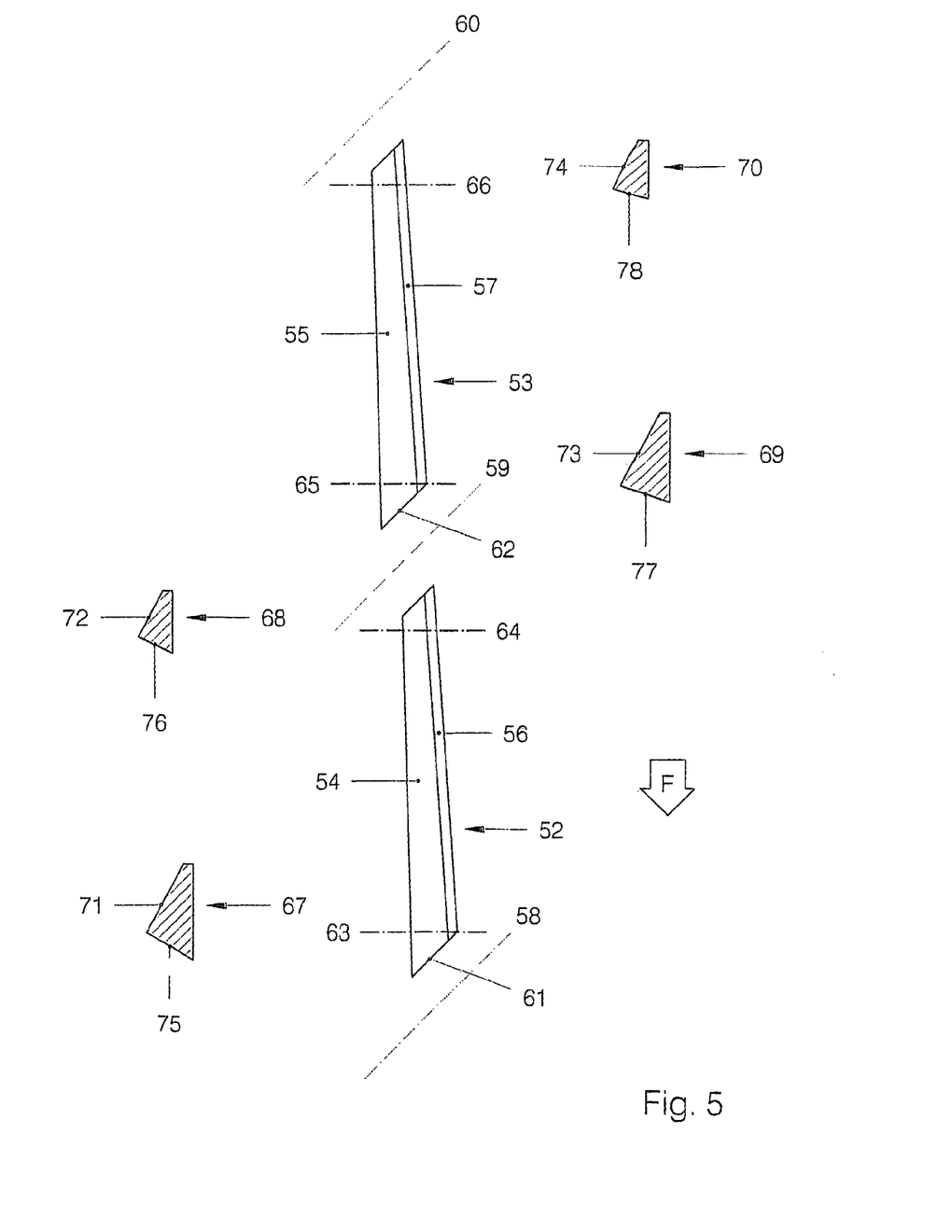
FIG. 5 is to illustrate the same situation having a superimposed ramp/step function.

FIGS. 4 and 5 of the drawing are to be used as an example of a modification of the thread of this type. Both figures of the drawing are very schematic, enlarged in scale, and greatly exaggerated in regard to the geometrical effect to be able to recognize the effects of the special machining at all. Only two sequential teeth of the particular thread of an imaginary hip joint socket are shown, and the thread base has been left out for the sake of simplicity.

FIG. 4 accordingly shows the portion of a thread course having a thread tooth 25 which adjoins a following thread tooth 26 in the screw-in direction F. Both thread teeth are placed geometrically on the exaggeratedly curved shell mantle of an invisible hip joint socket. While the flank of both thread teeth pointing toward the pole d (FIG. 8) is perpendicular to the shell mantle, the equator side flanks 27, 28 have an inclination in each case. Because of the trimming of the tooth head, both thread teeth have a particular front face 29, 30. The individual thread teeth result from the thread course by working out particular flutes, of which the centers are indicated in the drawing as dot-dash lines 31, 32, 33. Because of the diagonal course of the flutes, tooth cutting edges 34, 35 having a positive rake angle are formed on the particular tooth front. In order that, in spite of a constant thread pitch, a uniform height of the angle bisectors of the thread tooth is achieved, the partial flank angle pointing toward the socket equator b (FIG. 8) must have a pivot motion (e.g., the so-called B axis) superimposed along its extension according to the present invention. A continuously changing thread tooth profile is thus generated. In the figure of the drawing, two sectional images 40, 41 and 42, 43 of the two thread teeth on the section lines 36, 37 and 38, 39 are shown. Because of the selected extreme curvature of the shell mantle, the curved tooth base 48, 49, 50, 51 is tilted more and more strongly in its inclination toward the pole d (FIG. 8) of the hip joint socket. In the figure of the drawing, the individual angles of inclination of the thread tooth flanks 44, 45, 46, 47 pointing toward the equator b (FIG. 8) are implemented in spite of the exaggerated illustration by 26.25°, 26.91°, 27.61°, and 28.37°, and their particular differences may thus hardly be visually perceived. It is obvious that in real threads. implemented according to the present invention, in spite of the small angle change increments, significant orders of magnitude are achieved in addition. Typical partial flank curves show partial flank changes at a level of approximately 9° over the thread area, for example.

The thread design described above is not satisfactory per se, because jamming effects are to be expected during the screwing procedure due to the lack of clearance angles on the thread teeth and, in addition, the particular tooth cutting edge not projecting in relation to the thread tooth flank may not unfold an effect. To correct these problems, it is also suggested according to the present invention that the curve of the thread course have a function synchronized with the tooth sequence in the form of ramps and steps superimposed on it in such a way that a neutral angle or clearance angle and simultaneously an exposed position of the tooth cutting edge are formed behind the particular cutting edge formed on the tooth front. This modification is shown in FIG. 5.

FIG. 5 is based strongly on FIG. 4, the dimensions and geometrical effects shown here also being illustrated significantly exaggerated for the purpose of better understanding. As in FIG. 4, two thread teeth 52, 53 having diagonal flanks 54, 55 and front faces 56, 57 are shown. As previously, these thread teeth are separated from one another by introducing flutes, indicated here by dot-dash center lines 58, 59, 60. Section lines 63, 64, 65, 66 and the corresponding sections 67, 68, 69, 70 are again shown. The particular tooth base 75, 76, 77, 78 is identical in its angle—if this still exists—to those from FIG. 4. The flanks 71, 72, 73, 74 pointing toward the equator also maintain their partial flank angle and its pivot curve. However, a step function is superimposed on this curve in such a way that the thread tooth profile is now subject, behind its tooth front having the particular tooth cutting edge 61, 62, to continuous narrowing and height reduction in relation to the shell mantle of the hip joint socket. The lateral jump between the individual flanks of the thread teeth pointing toward the equator b (FIG. 8) and the height jump of the particular tooth head occurs in the area of the particular flutes in regard to the machining production and thus also on the finished product and is illustrated in the figure of the drawing by exposing the particular tooth cutting edge in relation to the preceding thread tooth. An effective cut of the tooth cutting edges is first implemented in this way and jamming of the thread teeth during screwing is securely suppressed.

The screw-in element according to the present invention, which is distinguished in that as shown in FIG. 8 the flank e of the thread tooth lying in the screw-in direction F has a constant angle and the other flank g of the thread tooth is subject to an angle change in the cited partial area, is particularly favorable in combination with a left-hand thread. At constant thread pitch, the equator-side flank becomes the shifting edge as the tooth is tilted toward the pole d. The tooth cutting edge i is then also favorably implemented on the equator-side flank. A left-hand thread thus results.

The jump function described above made of ramps and steps, which is superimposed on the thread course, is not producible using the typical turning methods. Therefore, it is hereby suggested that the machining be divided into at least two steps. Firstly the flowing contour of the corresponding thread tooth flank is produced using CNC turning, for example, as shown in FIG. 4. This is followed by a milling step for generating the particular superimposed function formed by ramp and step, which only has to remove relatively little material. In principle, this machining may also be executed using the so-called hobble turning method of the applicant, as is described in EP 1 051 131 A1 and EP 1 318 803 A1.

In regard to the practical implementation of the present invention, a very large bandwidth exists in regard to the tooth profile (tooth height, enclosed flank angle, tilt angle, shape and angle of the tooth head) and its curve (thread pitch, relative high reduction, change of the partial flank angle). A very flexibly usable means for the optimum adaptability of special threads, in particular of special threads which are curved or buckled in their extension, is provided by the present invention.

FIG. 6 shows a schematic illustration of an artificial hip joint socket 79 according to the prior art in a slightly enlarged scale. The example shown has a spherical contour of the curved shell mantle. Four peripheral tooth ribs 81, 82, 83, and 84 are shown, which are interrupted by a single flute 86. The other flutes have been left out for reasons of simplicity. The center axis of the hip joint socket is indicated by a dot-dash line 80 and the center of the flute by a dot-dash line 85. The negative inclination angle α is formed between the two. The inclination angle corresponds in its dimension to the pitch angle of the thread, so that the cutting edges formed on the thread teeth by the flute are transverse to the extension of the thread ribs in regard to the feed direction during screwing, and are thus neutral.

Figure 7:
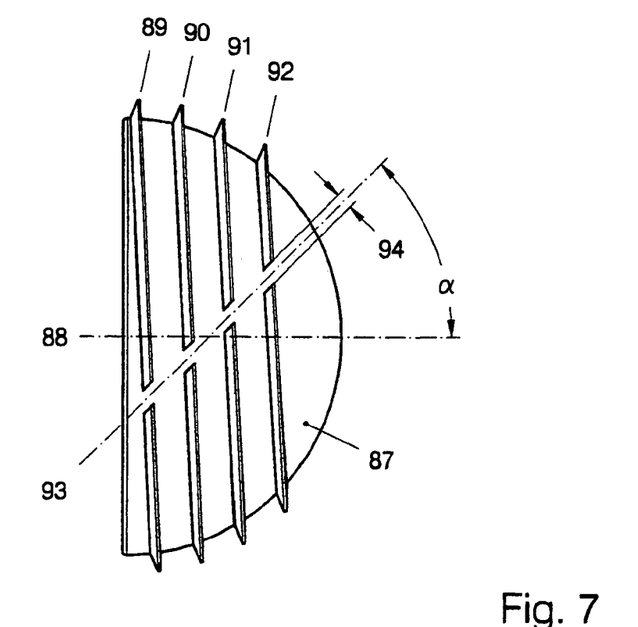
FIG. 7 shows a hip joint socket according to the present invention having a thread tooth profile tilted toward the socket pole and a negative inclination angle of the flute.

FIG. 7 shows an artificial hip joint socket 87 according to the present invention of identical size and shape. As previously, only one single flute 94 has been shown for reasons of simplicity. Illustrating a twist has been dispensed with because of the complexity of drawing it. The thread comprising four revolutions 89, 90, 91, and 92 has an asymmetrical tooth profile which is inclined toward the socket pole. This tilt direction causes—as explained above—equalization of the forces to be transmitted between implant and bony bearing. The flute is opposite in its angle to that of the thread pitch. It encloses an angle α of 45° with its dot-dash center line 93 to the axis 88 of the hip joint socket. The tooth cutting edges formed on the thread ribs are now on the rear of the thread ribs on the thread tooth flanks directed toward the socket equator and each have a strongly positive rake angle because of the flutes, which run strongly diagonally. Due to the more favorable placement of the tooth cutting edges in relation to the prior art, these come into effect fully in connection with the positive rake angle and thus cause a significant reduction of the screw-in torque and simultaneously an increase of the stripping reserve.

The invention claimed is:

1. A screw-in element comprising a pole, an equator, and seen in a cross-section passing through a screw-in axis a nonlinear lateral surface in at least one partial area and a thread groove and a thread lying at least in this partial area, said thread having a changing thread profile formed by thread teeth running along a line surrounding the screw-in element in a direction from the pole of the screw-in element to the equator of the screw-in element, a first flank of each thread tooth lying in a screw-in direction having a constant angle, wherein a second flank of each thread tooth faces the equator and is subject to an angle change in the at least one partial area, wherein the angle change of the second flank of each thread tooth occurs continuously, wherein in a cross-section passing through the screw-in axis the first flank of each thread tooth lying in the screw-in direction is perpendicular to the screw-in axis of the screw-in element, and wherein a cutting edge is implemented on the second flank of each thread tooth.

2. The screw-in element according to claim 1, wherein a curve of the thread teeth has a geometric function formed by at least one ramp and one step superimposed on the curve.

3. The screw-in element according to claim 2, wherein a height of the thread profile in relation to the lateral surface of the screw-in element is reduced in an area lying behind a particular tooth cutting edge.

4. The screw-in element according to claim 1, wherein the screw-in element is implemented as an implant.

5. The screw-in element according to claim 4, wherein the screw-in element is implemented as a hip joint socket having a non linear external shape seen in the cross-section passing through the screw-in axis.

6. A method for machining threads, which have a thread profile changing in at least a partial area, on a CNC machine, preferably a CNC lathe, the threads being machined at least in this partial area using at least two production steps and/or cycles, wherein in one of these production steps and/or cycles, an edge of a lathe chisel cutting first flank thread teeth assumes a fixed angle, and in another production step and/or cycle, the edge of the lathe chisel cutting second flank thread teeth is changed in angle during passage through a thread groove, wherein the threads are on a screw-in element comprising a pole, an equator, and seen in a cross-section passing through a screw-in axis a nonlinear lateral surface in the at least one partial area and the thread groove and the thread lying at least in this partial area, said thread having the changing thread profile formed by thread teeth running along a line surrounding the screw-in element in a direction from the pole of the screw-in element to the equator of the screw-in element, the first flank of each thread tooth lying in a screw-in direction having a constant angle, wherein the second flank of each thread tooth faces the equator and is subject to an angle change in the at least one partial area, wherein the angle change of the second flank of each thread tooth occurs continuously, wherein in a cross-section passing through the screw-in axis the first flank of each thread tooth lying in the screw-in direction is perpendicular to the screw-in axis of the screw-in element, and wherein a cutting edge is implemented on the second flank of each thread tooth.

7. The method according to claim 6, wherein one of the production steps and/or cycles essentially relates to one flank of the thread teeth and a part of a neighboring thread base, and another of the production steps and/or cycles essentially relates to another flank of the thread teeth and a part of the neighboring thread base.

8. The method according to claim 6, wherein the threads are machined using three different production steps and/or cycles, in which essentially a middle of the thread groove is machined using a third of the production steps and/or cycles and an angle setting is used for the lathe chisel which lies between the angle settings used for a first and a second of the production steps and/or cycles.

9. The method according to claim 8, wherein the third production step is executed first.

10. The method according to claim 6, wherein the angle change of the lathe chisel cutting the second flank thread teeth is performed continuously during passage through the thread groove.

11. The method according to claim 6, wherein the angle change of the lathe chisel is implemented using rotation of a B axis of the CNC machine, preferably a CNC lathe.

12. The method according to claim 6, wherein first a path to be described by a cutting radius center point of the lathe chisel during travel of the lateral surface, to be implemented in the form of a thread groove base, of the screw-in element to be produced is calculated, this path is converted using a particular offset for X and Z in regard to a distance of a blade radius center point of the lathe chisel from the rotation center point of a B axis of a compound slide and for B in relation to an angular difference between a blade of the lathe chisel and a zero setting of the B axis and applied in a CNC program, and a cutter center line is used in a workpiece description whose absolute value corresponds to a blade radius of the lathe chisel.

13. The method according to claim 6, wherein relative movement between workpiece and tool has a ramp and step function synchronized with a tooth sequence superimposed on the ramp and step function.

14. The method according to claim 13, wherein chip removal is performed using milling.

* * * * *